United States Patent [19]

Gentelia et al.

[11] Patent Number: 5,300,070
[45] Date of Patent: Apr. 5, 1994

[54] ELECTROSURGICAL TROCAR ASSEMBLY WITH BI-POLAR ELECTRODE

[75] Inventors: John S. Gentelia, Madison; Frank R. Williams, Frankfort; William C. Wheatley, Utica; Ernesto G. Sevilla, Herkimer; Sharyn E. Longo, Frankfort; Deborah E. Forbey, Smyrna, all of N.Y.

[73] Assignee: Conmed Corporation, Utica, N.Y.

[21] Appl. No.: 901,024

[22] Filed: Jun. 19, 1992

Related U.S. Application Data

[63] Continuation-in-part of Ser. No. 853,149, Mar. 17, 1992.

[51] Int. Cl.⁵ .............................................. A61B 17/36
[52] U.S. Cl. ...................................... 606/45; 606/39; 604/164; 604/264
[58] Field of Search ...................... 606/34–48, 606/167, 184, 185; 604/21, 22, 33, 164, 264, 156, 157, 158

[56] References Cited

U.S. PATENT DOCUMENTS

| | | | |
|---|---|---|---|
| 3,595,239 | 7/1971 | Petersen | 606/45 |
| 3,964,487 | 6/1976 | Judson | 606/39 |
| 4,043,342 | 8/1977 | Morrison, Jr. | 606/48 |
| 4,550,727 | 11/1985 | Rexroth | 606/39 |
| 4,580,562 | 4/1986 | Goof et al. | 606/39 |
| 4,622,966 | 11/1986 | Beard | 606/45 |
| 4,716,897 | 1/1988 | Noguchi et al. | 606/39 X |
| 4,785,807 | 11/1988 | Blanch | 606/45 |
| 4,788,977 | 12/1988 | Farin et al. | 606/39 |
| 4,793,345 | 12/1988 | Lehmer | 606/39 |
| 4,986,814 | 1/1991 | Burney et al. | 604/164 |

Primary Examiner—Peter A. Aschenbrenner
Attorney, Agent, or Firm—Larson & Taylor

[57] ABSTRACT

A trocar assembly includes an elongate trocar device and a surrounding cannula. The trocar device incorporates an electrosurgical cutting element which is used to make a guide hole for the cannula and thus enables the remainder of the trocar assembly to enlarge the puncture. The cutting element comprises a bi-polar electrode assembly. An electronic control circuit senses the current flow to the cutting element and, when the trocar device breaks through the wall of the body cavity being cut into, this circuit cuts off the connection to the associated electrosurgical generator. Further control circuitry prevents a surgeon from resuming electrosurgery until a predetermined time period has elapsed. Multiple trocars of different diameters are provided for the same assembly.

8 Claims, 5 Drawing Sheets

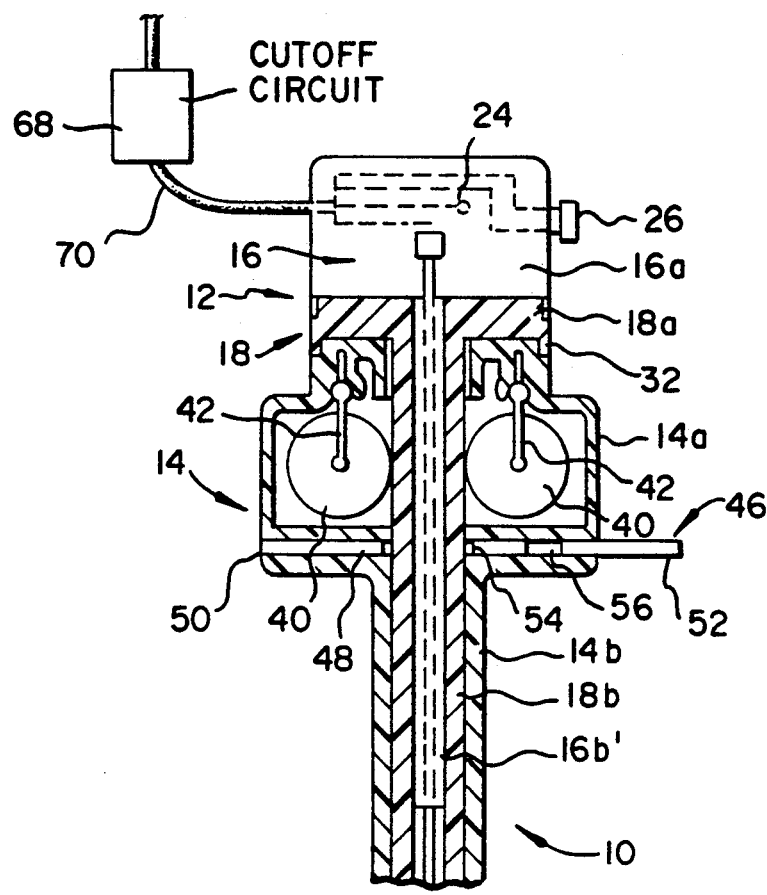
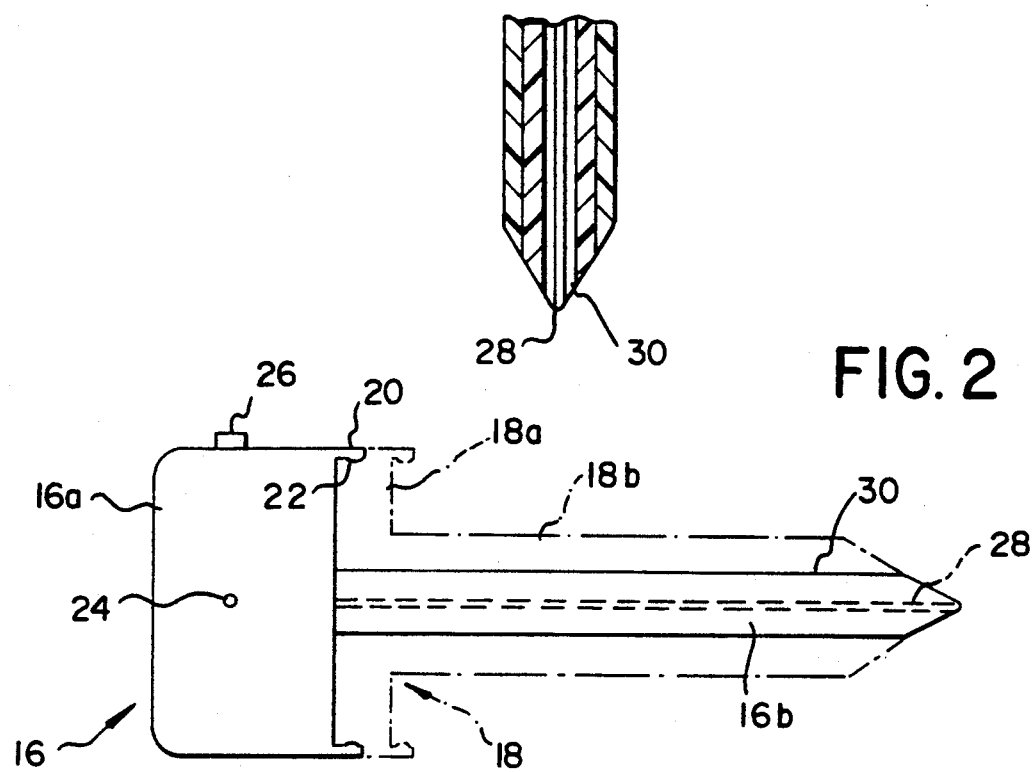

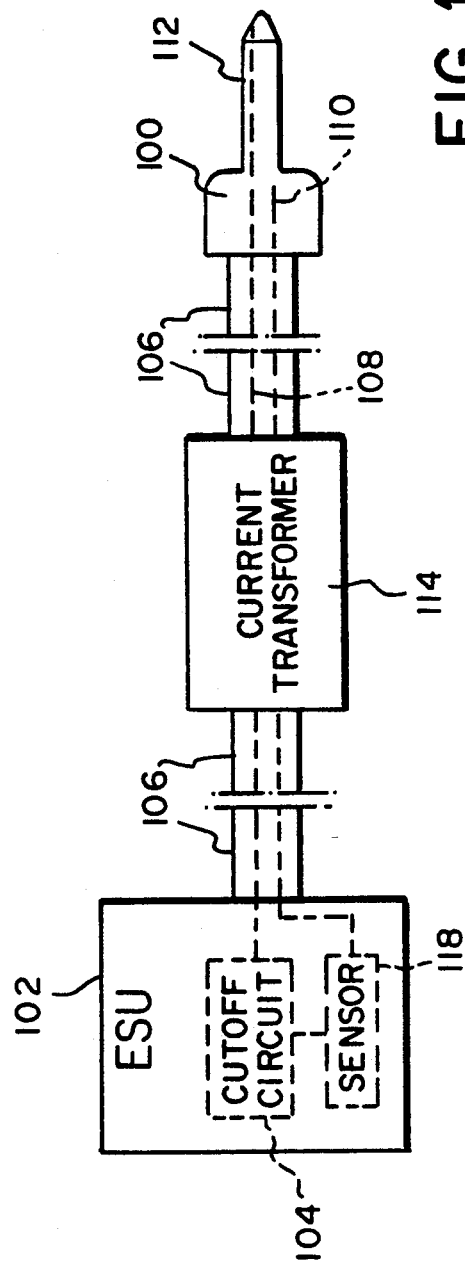
FIG. 10
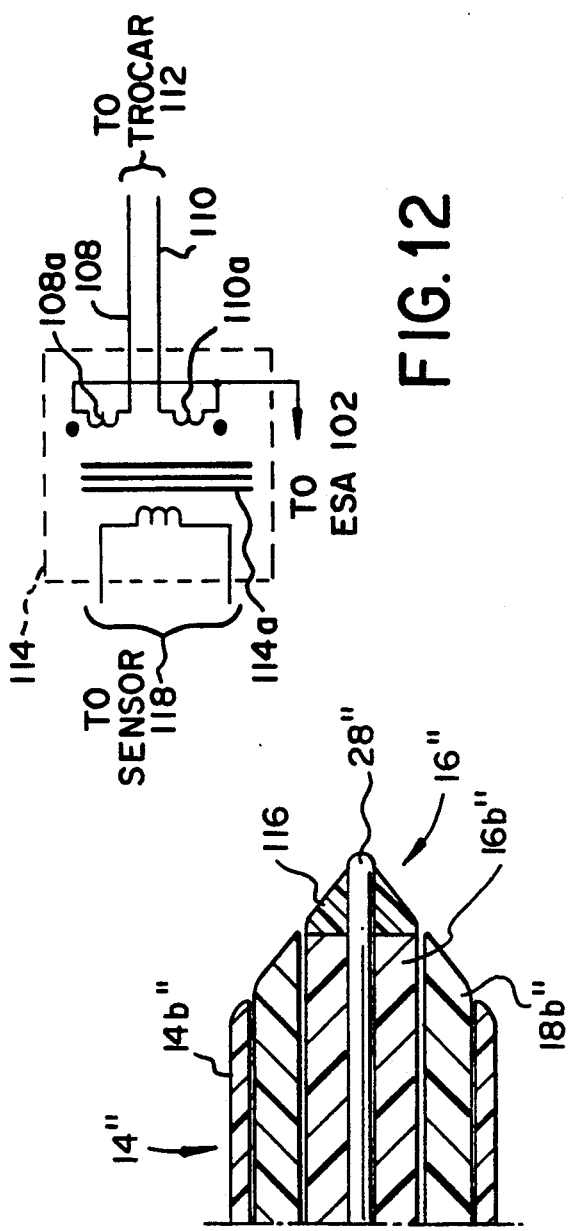
FIG. 12
FIG. 11

ELECTROSURGICAL TROCAR ASSEMBLY WITH BI-POLAR ELECTRODE

CROSS REFERENCE TO RELATED APPLICATION

This application is a continuation-in-part of our co-application Ser. No. 07/853,149, filed Mar. 17, 1992, and entitled ELECTROSURGICAL TROCAR ASSEMBLY.

FIELD OF THE INVENTION

The present invention relates to trocar devices or assemblies used in surgery and, more particularly, to an electrosurgical trocar device or assembly.

BACKGROUND OF THE INVENTION

Surgical procedures such as laparoscopic procedures require the surgeon to create one or more punctures in the anatomy of the patient to enable a guide tube, referred to as a cannula, to be sited and thereby enable surgical instruments to be passed down through the cannula into the patient in order to carry out the intended procedures.

One method of accomplishing this is the open or "Hussan" method wherein an incision is made in the desired area to accommodate the cannula and sutures are put around the cannula to close the gap left by the incision. Sutures are also made from the skin to cannula to assist in holding the cannula in place. This technique is used primarily (but not exclusively) in situations wherein other abdominal surgeries pose potential adhesion complications. Such complications can cause an unintended puncture in the bowel or in other organs.

A second method involves the use of a mechanical trocar device which comprises the combination of a trocar and a cannula. The trocar basically comprises a rod or shaft having a very sharp cutting edge or point at one end thereof and is enclosed within the tubular cannula. In some devices, the cannula incorporates some kind of safety mechanism, such as a shield, over the cutting tip prior to use to reduce the chance of unintended punctures. Trocar devices characteristically require substantial force to drive the cutting end or tip through, e.g., the abdomen wall and as a result, trocar devices can be hard to control. A separate trocar device, i.e., comprising a trocar and cannula, is used for each puncture site.

SUMMARY OF THE INVENTION

In accordance with the invention, a trocar device or assembly is provided which overcomes the problems with prior art trocar devices discussed above. The trocar device of the invention comprises an electrosurgical cutting element, which, in common with electrosurgical cutting instruments commonly referred to as electrosurgical "blades," provides cutting of tissue through the transmission of radio frequency electrical energy to the area to be cut. The trocar device of the invention uses electrosurgery to make the guide hole for the cannula and thus enables the remainder of the cannula assembly to enlarge the puncture. This greatly reduces the force required as compared with mechanical trocar devices. This reduction in force enables an even, constant insertion pressure to be exerted, thereby allowing substantially greater control and reducing the chances of an unintended puncture. Further, the use of electrosurgery eliminates the need for a sharp point as is required in mechanical trocar devices, thereby allowing multiple uses of the same trocar.

In accordance with a preferred embodiment of the invention, the electrosurgical cutting element comprises a bi-polar electrode assembly. The bi-polar electrode assembly comprises first and second independent, mutually insulated electrodes, one of which carries the radio frequency current and the other of which provides a return path to ground. Although a single electrode arrangement can be used wherein a single electrode carries the radio frequency current and a return to ground is provided by, e.g., a ground pad placed in a remote area of the body, the bi-polar electrode assembly ensures that the ground circuit is disposed in close proximity to the radio frequency cutting point.

The electrosurgical cutting element is, in use, connected to a conventional electrosurgical generator or other source of radio frequency (r.f.) power or energy (the term electrosurgical generator being used herein to refer to any suitable source for driving the electrosurgical cutting element) and a further important feature of the trocar assembly of the invention is in the provision of an electronic control (cutoff or shutdown) circuit for sensing current flow and, when the trocar breaks the wall of the body cavity involved, for opening or cutting off the connection to the electrosurgical generator. This feature substantially eliminates any chance of an unintended puncture.

In addition, further circuitry is preferably provided which requires that the operator (surgeon) release a control switch for a predetermined time period prior to resuming surgical operations so that power is again provided to the electrosurgical cutting element only as the result of a conscious decision on the part of the operator. As a result, inadvertent operation of the cutting element, and thus possible inadvertent puncturing of an organ wall, are combatted or avoided. Advantageously, an indicator such as a light emitting diode (LED) is used to indicate that the generator is supplying power to the cutting element (preferably by providing a continuous light output) and to also indicate the predetermined time period before electrosurgery can be resumed (preferably by providing a blinking or intermittent light output).

A further important feature of the invention involves the provision of multiple trocars as part of a trocar assembly or kit, independently of whether or not an electrosurgical cutting element is used. The provision of multiple trocars enables the same basic device to provide punctures or openings of different diameters. The trocars can be very simple in construction and thus can be made to be low cost disposable items.

As discussed above, one aspect of the invention concerns the provision of a control (shutoff) circuit for shutting off the RF power supplied to the trocar, upon penetration of the trocar through, e.g., the abdomen wall, by sensing the change in load impedance when this happens. This change can be detected in a number of ways including monitoring the current, the voltage or the phase shift. As is discussed below, for reasons of simplicity and economy it is desirable to locate as much of the control circuitry as possible in the electrosurgical generator (ESU) or an auxiliary control box. The disadvantage of doing this is that, at the frequencies involved in electrosurgery, the cable connected to the trocar presents a sizeable and varying "leakage" impedance that complicates the task of providing reliable detection of the shut-off point, as the signal-to-noise ratio of the detected signal deteriorates.

In accordance with a further aspect of the invention, in order to deal with this problem, means are provided for counteracting the effects of the "leakage" impedance described above. Various means can be used for this purpose including the provision of a sample and hold circuit for determining initial conditions prior to contact being made (and, of course, the critical sensing elements can be located close to the trocar end of the cable to minimize the effect). However, according to a preferred embodiment of this aspect of the invention, a reference wire or lead is included in the connecting cable for the trocar which is connected in parallel with the "hot" wire or lead (i.e., that carrying the RF current to the cutting element of the trocar) but which is not connected to the cutting element. With this arrangement, the control circuit senses the difference between the load conditions seen by the "hot" (current carrying) wire and the reference wire. The reference wire or lead can be a dedicated lead or can be a wire or lead already used in the system to perform some other function at the trocar end such as switching or indication. In an advantageous implementation of this embodiment, a current transformer is used to sense the change in load impedance. In this embodiment, the current carrying wire or lead and the reference wire or lead are passed through the core of the current transformer in such a way as to oppose each other so that the leakage current is substantially neutralized.

In accordance with a further embodiment, the cutting element, whether monopolar or bipolar, is provided with a specialized high temperature resistant insulating portion, made of Teflon (polytetrafluoroethylene), a high temperature ceramic or the like, adjacent to the distal tip of the cutting element.

It is noted that a major advantage of the electronic surgical device of the invention is that a cutoff or protective action can be instituted as soon as the tip emerges through the cavity wall in question based on sensing the corresponding change in impedance. This cutoff is substantially immediate and the danger of the cutting element inadvertently puncturing an organ within the cavity is substantially eliminated. This contrasts with mechanical trocar devices which provide for release of a protective sheath for covering the cutting blade only after the body of the trocar device has fully penetrated the cavity wall.

Other features and advantages of the invention will be set forth in, or apparent from, the following detailed description of preferred embodiments of the invention.

BRIEF DESCRIPTION OF THE DRAWINGS

FIG. 1 is a side elevational view, partially in cross section, of a trocar assembly in accordance with a preferred embodiment of the invention;

FIG. 2 is a side elevational view of one of the trocars of FIG. 2, with the second trocar being shown in phantom lines;

FIG. 10 is a schematic circuit diagram of a further embodiment of the invention; and FIG. 11 is a partial cross sectional view similar to that of FIG. 4 illustrating yet another embodiment of the invention; and FIG. 12 is a schematic circuit diagram of the current transformer of the embodiment of FIG. 10.

DESCRIPTION OF THE PREFERRED EMBODIMENTS

Referring first to FIG. 1, there is shown a schematic side elevational view, partially in section, of a trocar assembly which is generally denoted 10. The trocar assembly 10 basically comprises a multi-element trocar 12 and a cannula 14.

Figure 5:
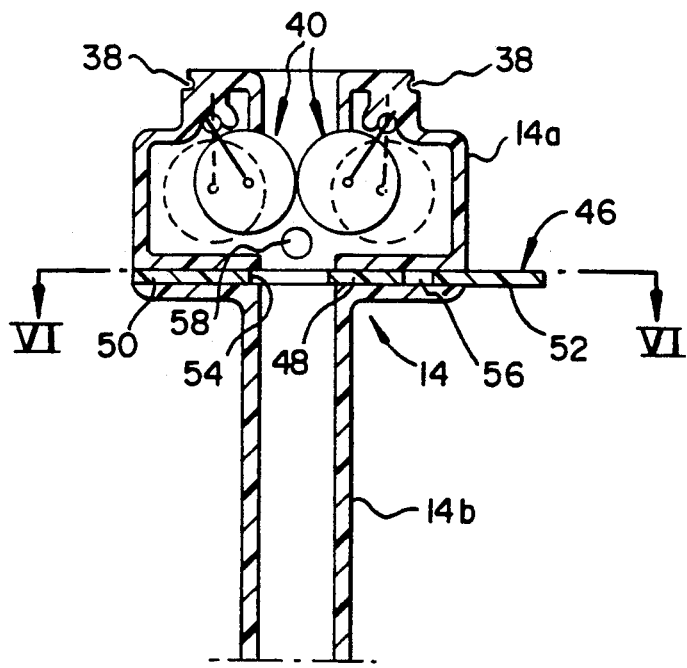
FIG. 5 is a partial cross sectional view of the cannula of the trocar assembly of FIG. 1 showing the operation of the seal rollers.
Figure 6:
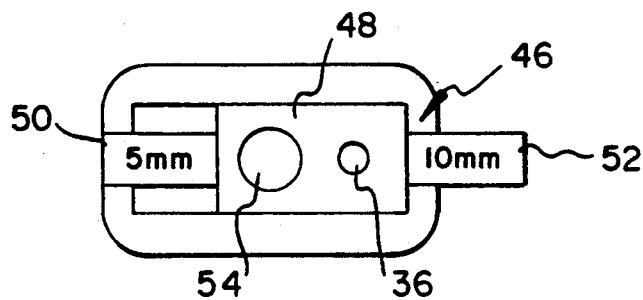
FIG. 6 is a cross sectional view taken generally along line VI—VI of FIG. 5.

The multi-element trocar 12 includes a central or inner trocar member 16 (perhaps best seen in FIGS. 2 and 4) comprising a head portion 16a and a shaft or rod portion 16b, and an outer trocar member 18 (perhaps best seen in FIGS. 3 and 4) which comprises a head portion 18a and a hollow shaft portion 18b and which slides onto and releasably engages trocar member 16. As shown, head portion 18a of trocar member 18 is affixed to head portion 16a while shaft portion 18b surrounds shaft or rod portion 16b. The cannula 14, which is also shown in FIGS. 5 and 6, comprises a head or upper housing portion 14a and a guide tube or cannula portion 14b. As shown, head portion 14a is affixed to the head portion 18a of the outer trocar member 18 and the cannula portion 14b surrounds hollow shaft portion 18a.

Figure 3:
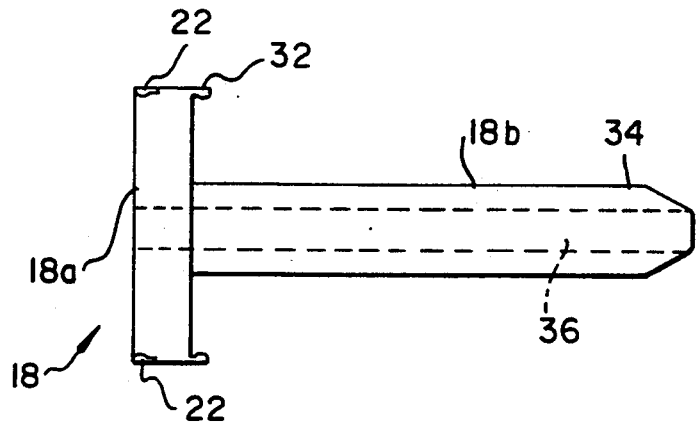
FIG. 3 is a side elevational view of the second, outer trocar of FIG. 1.
Figure 4:
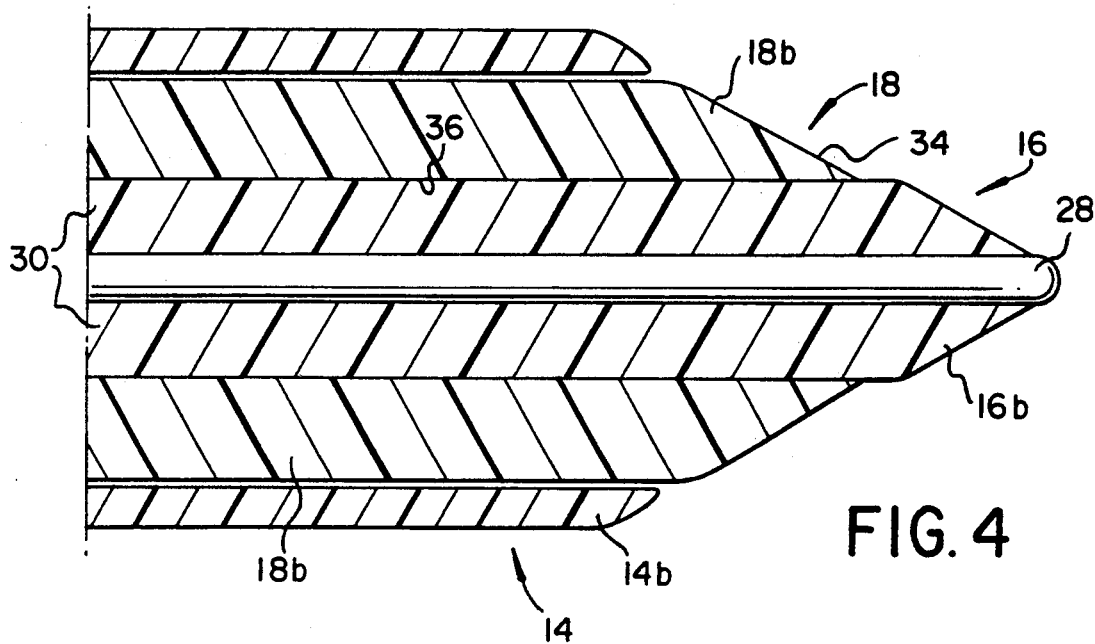
FIG. 4 is a cross section view, to an enlarged scale, of the distal or free end of the trocar assembly of FIG. 1.

Considering the inner or central trocar member 16 in more detail and referring to FIGS. 1, 2 and 4, head portion 16a is generally cylindrical in shape and includes an outwardly extending locking member or skirt 20 having a shaped rim or circumferential lip portion which is adapted to be received in a corresponding recess 22 in head portion 18a of outer trocar 18 (see also FIG. 3) so as to provide a releasable snap fit, as is indicated in phantom lines in FIG. 2. It will be understood that a similar releasable connection can be provided between the trocar members 16 and 18 using other suitable connecting arrangements.

Head portion 16a is also provided with an indicator light or lamp 24 for indicating the operating state of the device as explained below and a reset pushbutton switch 26 which resets the electronic circuitry described below.

The shaft portion 16b of central trocar member 16 comprises a central metal rod 28 and an outer insulating trocar shaft or tube 30. In a specific exemplary embodiment, rod 28 is made of stainless steel and is about 0.075 inches in diameter while trocar shaft 30 is made of a plastic, ceramic or any like material capable of providing the appropriate temperature resistance as well as has a relatively low coefficient of friction and has an outside diameter of about 3/16 of an inch or 5 mm. The distal end of trocar shaft 30 is tapered as illustrated so as to enable ready insertion thereof into a small hole "burned" through the wall in question by rod 28.

Electrical power is provided to rod 28 through an electrical circuit located in head portion 16a and discussed in more detail below in connection with FIG. 7. This circuit, which is also shown in dashed lines in FIG. 1 includes indicator lamp 24 and switch 26.

Referring to FIG. 3, the head portion 18a of the second or outer trocar member 18 is also cylindrical in shape and, as noted above, includes a circumferential recess 22 for receiving locking or latching member 20. A similar locking or latching member or skirt 32 having rim or circumferential lip is provided at the other end of head portion 18b, as shown. The shaft portion 18b comprises a tubular trocar shaft 34 having a central bore 36 therein through which the central trocar shaft 30 extends. The distal end of trocar shaft 34 is tapered and as shown in FIG. 4 (and in FIG. 1), the overall taper provided by trocar shafts 30 and 34 is continuous or substantially continuous. Trocar member 18 does not contain any active components and in an exemplary embodiment has an outside diameter of about 13/32 inches or 10 mm and an inside diameter about 7/32 inches, i.e., a diameter just slightly larger than the outer diameter of inner trocar shaft 30. However, it is to be understood that outer trocar members of different sizes can be used and that a set of such trocar members can be provided which would selectively be slipped onto and over inner trocar shaft 30 to provide openings of different sizes in the wall of the abdomen or other organ. It will be appreciated that such outer trocars, which, as noted above, contain no active parts, are quite simple in construction and inexpensive to manufacture.

Referring now to FIGS. 1, 5 and 6, it will be seen that the head portion 14a of the cannula member 14 is hollow in construction and includes a shaped circumferential recess 38 in the upper or proximal end thereof in which reciprocally shaped circumferential locking member 32 of outer trocar member 18 is received so as to provide a snap fit between members 14 and 18.

Disposed within the head portion 14a of cannula member 14 are a pair of sealing rollers or rolls 40 which are suspended from the upper or proximal end wall of head portion 14a by springs 42 that bias the rolls 40 toward each other so as to close off an opening 44 in that proximal end wall, as shown in solid lines in FIG. 5. Inserting the shaft portions 16b and 18b of trocar members 16 and 18 down into opening 44 causes rolls 40 to be forced apart and to assume the positions shown in FIG. 1 and in dashed lines in FIG. 5. Reference is made to our commonly assigned copending application Ser. No. 07/846,386, filed on Mar. 5, 1992, and entitled LAPAROSCOPIC CANNULA for a further description of arrangement for permitting insertion of a trocar while shutting off the opening for the trocar after the trocar is removed.

A selectable seal device 46 is best seen in FIG. 6. The seal device 46 includes a flat sealing member 48 having pull tabs 50 and 52 at opposite ends thereof and openings 54 and 56 of different sizes so as to accommodate trocars of different diameters. In the exemplary embodiment illustrated, the openings 54 and 56 are designed to receive the 10 mm trocar 18 and the 5 mm trocar 16 and tabs 50 and 52 are marked accordingly. Thus, with 10 mm tab 52 pulled out so that sealing member 48 is moved to the right as shown in FIG. 6, the 10 mm opening 54 is brought into alignment or registration with opening 44 so that the 10 mm outer diameter trocar 16 can be inserted therethrough as indicated in FIG. 1. Sealing member 48 is disposed in a slot in housing portion 18a and is slidable therein as described above. It will be appreciated that the embodiment just described is exemplary only and that, for example, the openings in sealing member 46 can be different in number and sizes so as to accommodate surgical instruments of various sizes during surgery.

As shown in FIG. 5, an opening 58 is provided in head or housing portion 14a which enables irrigation fluid to be supplied to the puncture site through cannula shaft 14b, when the trocars 16 and 18 are removed.

Figure 7:
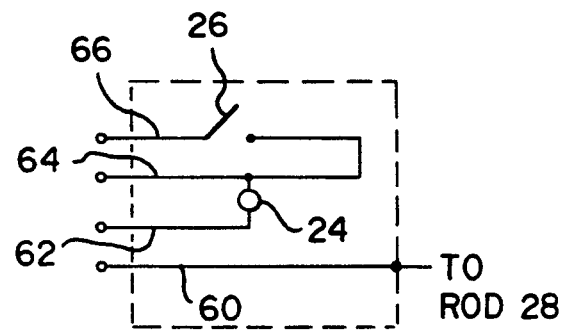
FIG. 7 is a schematic circuit diagram of circuitry incorporated into the cannula of FIG. 1.

Referring to FIG. 7, there is shown a schematic circuit diagram of the electrical circuitry contained within the head portion 16a of the m in trocar 16 (this circuitry also being shown in dashed lines in FIG. 1). As illustrated, four input leads or connections, denoted 60, 62, 64, and 66 are provided, one of which, lead 60 is the "hot" lead directly connected to electrosurgical rod 28. Leads 64 and 66 provide a current input and return path for switch 26 while lead 62 connects optional indicator lamp 24 to lead 64.

Figure 8:
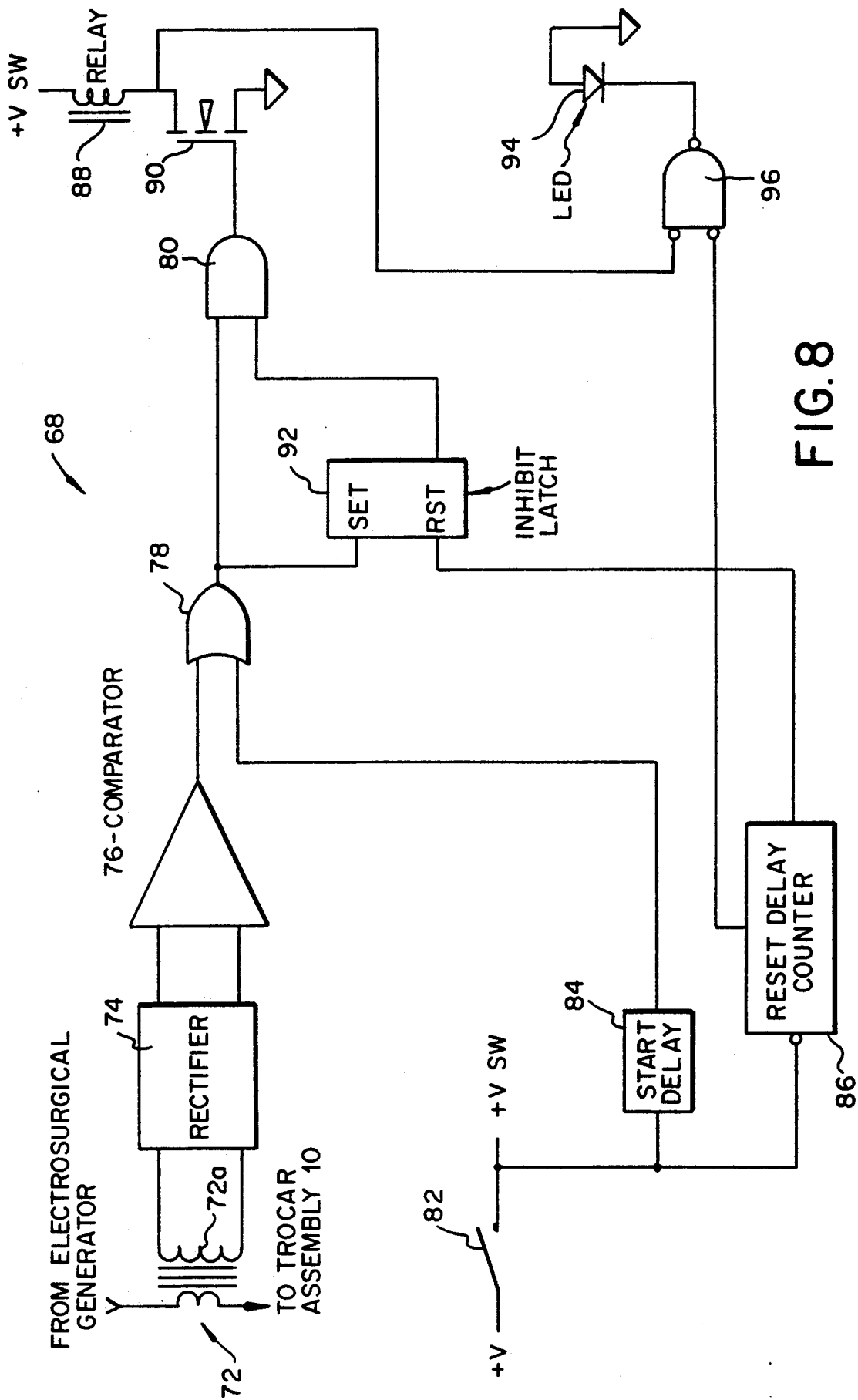
FIG. 8 is a schematic circuit diagram of the cutoff circuit of FIG. 1.

Referring to FIG. 8, a preferred embodiment of the cutoff circuit for the electrosurgical generator is shown. As indicated in FIG. 1, the cutoff circuit, which is generally denoted 68, can be a separate package or unit connected into the cable 70 or in another connection between the electrosurgical generator (not shown) and the trocar assembly 10. Alternatively, the circuit can be built into the electrosurgical generator. The cutoff circuit 68 of FIG. 8 includes a current transformer 72 connected to the generator output line (which can correspond to cable 70 of FIG. 1) so as to sense or monitor the current flow from the electrosurgical generator (not shown) to the trocar assembly 10. The secondary winding 72a of transformer 72 is connected to a rectifier 74 which produces an output voltage that is a function of the current level. Rectifier 74 is connected to an adjustable voltage comparator 76 which determines the cutoff current by comparing the output voltage produced by rectifier 74 with a predetermined reference level. The output of comparator 76 is connected to one input of an OR gate 78 the output of which is connected to an AND gate 80. The functions of the gates 78 and 80 are described in more detail below.

A control switch 82 is provided for controlling energizing of the electrosurgical generator. This switch can correspond to switch 26 described above and is controlled by the surgeon. A pair of delay networks, a start delay circuit 84 and a reset delay counter circuit 86, are connected to switch 82 in parallel with each other. Start delay circuit 84 begins timing out its associated delay when switch 82 is closed while reset delay counter circuit 86 begins timing out its associated delay when switch 82 is opened. The significance of delay circuits 84 and 86 is explained below.

The output of start delay circuit 84 is connected to the other input of OR gate 78 and the delay provided allows time for the surgeon to start a cut after activating the switch 82. Thus, when switch 82 is closed the output of start delay circuit 78 provides for closing of a control relay 88 for the electrosurgical generator so as to turn on the electrosurgical generator. Relay 88 is connected to the output of AND gate 80 through an IGFET switch 90 provided so as to ensure that the appropriate relay switching levels are maintained. After delay circuit 84 times out, the operation of relay 88 is controlled by the output of the current sensor 72 and, more particularly, by the output of comparator 76. Thus, if this output drops below the level set within comparator 76, relay 88 is opened and power to the electrosurgical generator is cut off.

The cutoff circuit 68 also includes an inhibit latch 92 which includes a first, set input connected to the output of OR gate 78, a second, reset input connected to the output of reset delay counter circuit 86 and an output connected to the other input of AND gate 80. When the sensed current drops below the preset or predetermined reference value dictated by comparator 76, this is reflected at the set input of inhibit latch 90 and latch 90 is set (in addition to the control relay 88 opening as mentioned above). The inhibit latch 90 will remain set until the switch 82 is opened for the reset delay period, i.e., the period of reset delay counter circuit 86, which is approximately three seconds in a specific exemplary embodiment. The reason for this provision is that the normal current level will drop when an initial puncture is made and the intention here is to ensure that the electrosurgical cutting element rod 28 will not be used to cut again until the surgeon intentionally provides for the electrosurgical generator to be turned back on, i.e., after the three second delay provided by reset delay counter circuit 86. As noted above, opening of switch 82 starts the inhibit or reset delay period, and during this delay period it is not possible to turn the generator on. In this regard, reactivating switch 82 resets the delay period, so that in order to turn on the electrosurgical generator, switch 82 must be released or opened, and left open for the full delay period, in order to reset the inhibit latch circuit 92. Of course, with inhibit latch 92 reset, the circuit operates as set forth above and the surgeon can begin cutting again.

In order to alert the surgeon to the fact that the reset delay period is being timed out, an intermediate stage of the counter of the reset delay counter circuit 86 is used to cause an indicator light or lamp (e.g., a LED) 94 to blink during the inhibit delay period. (Again, indicator lamp 94 can correspond to indicator lamp 24 of FIG. 1.) Considering this operation in more detail, a negative OR or NOR gate 94 is provided which has a first input connected to the output of IGFET switch 90, a second input connected to the aforementioned intermediate stage of reset delay counter 86 and the output connected to the LED 94. When the output of switch 90 is low, meaning that control relay 88 is actuated and the electrosurgical generator is turned on, LED 94 will also be continuously on to provide an indication to the surgeon that the generator is on. Further, as set forth above, when the generator is off but the reset delay period is being timed out, the intermediate stage of reset delay counter 86 will provide a pulsed signal to NOR gate 96 which will cause blinking of LED 94 during this period. As explained previously, when this period is up, as indicated by the fact that LED 94 is no longer blinking, the surgeon will know that the can close switch 82 and resume surgery.

Figure 9:
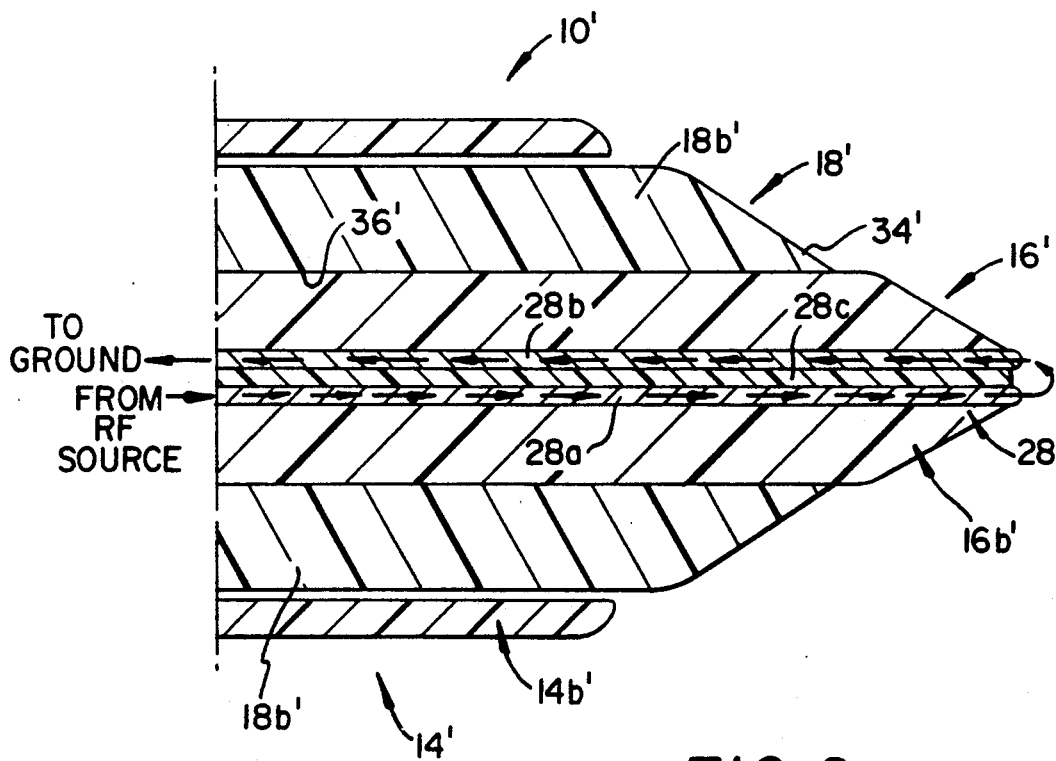
FIG. 9 is a partial cross-sectional view similar to that of FIG. 4 illustrating a further embodiment of the invention.

Although the cutting element or electrode assembly of the inner trocar can comprise a single electrode rod 28 as illustrated in FIG. 4, the electrode assembly can also comprise a bi-polar electrode assembly as indicated at 28' in FIG. 9. More specifically, such a bi-polar electrode assembly comprises, as illustrated in FIG. 9, a pair of independent, mutually insulated electrodes 28a and 28b separated by insulation 28c. As shown, electrode 28a is connected to the electrosurgical generator (not shown) and carries the r.f. current while electrode 28b provides a return path to ground. This is in contrast to the embodiment of FIG. 4, wherein rod electrode 28 carries the r.f. current and the return to ground path could be provided, e.g., by a conventional ground pad (not shown) placed in a remote area of the body. The bi-polar electrode assembly 28' of FIG. 5 is advantageous in that the ground circuit (provided by ground return electrode 28b) is in close proximity to the r.f. cutting point and it is not necessary to provide a ground return through the body and thus risk the possibility of internal burning. However, it is noted that such a conventional ground pad (not shown) can also be provided with the embodiment of FIG. 9, as a back-up.

As discussed above in connection with FIG. 8, electronic trocar of the invention is adapted to shut off the RF power supplied to the trocar upon penetration of the trocar tip through the wall of the body cavity in question, e.g., the abdominal wall, by sensing the change in load impedance. As was also mentioned previously, this sensing or detecting of a change in load impedance can be achieved by monitoring current, voltage or phase shift. The associated control circuitry is advantageously incorporated in the generator itself or in a separate control box or control unit 68 as explained above, and one problem that is encountered in doing this is that, at the frequencies involved, the connecting cable (cable 70 of FIG. 1) presents sizeable and varying "leakage" impedance that makes reliable detection of the shut off point difficult as the signal to noise ratio of the detected signal deteriorates.

Referring to FIG. 10, the "leakage" impedance problem is solved by the illustrated circuit. FIG. 10 illustrates a system wherein a trocar assembly 100 corresponding to trocar assembly 10 or 10' described above is connected to an electrosurgical unit or generator (ESU) 102 which includes a cutoff or shutdown circuit 104 that can, e.g., correspond to the circuit discussed above in connection with FIG. 8. A cable 106 connects ESU 102 to trocar assembly 100 and includes a connecting wire or conductor 108 which corresponds to the "hot" wire of the embodiments discussed above (e.g., conductor 60 of FIG. 7).

According to this embodiment of the invention, a reference wire or conductor 110 is also provided in cable 106 in parallel with the wire 108 carrying the RF current to the trocar 100 but is not connected to the cutting element 112. As a result, the control circuitry will then sense the difference between the load conditions seen by the "hot" wire or lead 108 and the reference wire or lead 110. In the exemplary embodiment illustrated, a current transformer 114 is used to sense the change in load impedance, as shown in FIG. 12 which is a schematic circuit diagram of the current transformer, and windings 108a and 110a formed from the current carrying wire 108 and reference wire 110 respectively are passed through the core 114a of the current transformer 114 and wound in opposition therein as indicated in FIG. 12, i.e.,; in such a manner as to oppose each other, thereby essentially neutralizing the effect the leakage current in the output sensed by current sensor 118. It is noted that the reference wire or lead 110 can be a separate wire dedicated to that purpose or can be a wire used for some other function such as switching or indication at the trocar end (and thus corresponding to the wires or conductors discussed above).

As mentioned above, other techniques can be used to counteract the effect of the leakage impedance, including the use of a sample and hold circuit (not shown) for sensing the initial conditions before contact is made or by locating the critical sensing elements close to the trocar end of the cable.

Referring to FIG. 11, a further embodiment of the trocar tip is illustrated. This embodiment is similar to that of FIG. 4 and like elements are given the same reference numerals with double primes attached. This embodiment differs from that of FIG. 4 (and FIG. 9) in that the tip, denoted 116, of the shaft portion 16b″ of central trocar member 16″ is made of a high temperature resistant material such as Teflon, a high temperature ceramic or the like. Stated differently, shaft 16b″ is of a two part construction including a high temperature tip 116. This construction enables the trocar tip to better withstand the high temperatures generated during surgical procedures. It will, of course, be appreciated that although this embodiment has been described as a modification of the embodiment of FIG. 4, such a high temperature tip can also be provided with the bi-polar embodiment of FIG. 9.

In an implementation of the electronic trocar shutoff circuit such as that of FIG. 10 wherein a reference lead is used in the cable to neutralize the effects of leakage, it is important to ensure that the reference lead is present, e.g., that, in FIG. 10, lead 110 has not been broken or pulled out from the trocar 100. One way of doing this is by utilizing a current sensor such as that indicated schematically at 118 in FIG. 10 which monitors the leakage current flowing in the reference lead 110. This will check for an open lead. If the lead is shorted to the active wire the shutoff sensor 118 will not sense any current and will turn off the electrosurgical generator. A short to the abovementioned switch lead and/or indicator lead can also upset the balance of the current sensor 118. Such a short can be detected by sensing the presence of the generator output voltage on these leads.

Although the present invention has been described relative to specific exemplary embodiments thereof, it will be understood by those skilled in the art that variations and modifications can be effected in these exemplary embodiments without departing from the scope and spirit of the invention.

What is claimed is:

1. An electrosurgical system comprising a radio frequency power source, an electrosurgical trocar device connected to said power source and including a cutting element having a cutting tip and a cut-off circuit for sensing the load impedance at the cutting tip of said trocar device and for interrupting the connection between the trocar device and the power source responsive to a change in said load impedance, said cutting element being connected to said power source through a current carrying conductor of a scale presenting a leakage impedance at the operating frequencies of said power source and said system further including means for counteracting the effect of the leakage impedance presented by the cable so that the load impedance sensed by said cut-off circuit is substantially free of the effect of said leakage impedance.

2. A system as claimed in claim 1 wherein said means comprising a reference conductor incorporated in said cable and arranged so as to extend along said current carrying conductor.

3. A system as claimed in claim 2, wherein said reference conductor and said current carrying conductor are connected to said source through a current transformer having a transformer core and are wound in opposition on the transformer core.

4. A system as claimed in claim 1 wherein said reference conductor is arranged so as to be permanently electrically disconnected from the cutting element o the trocar device.

5. An electrosurgical system comprising a radio frequency power source, an electrosurgical trocar device connected to said power source and including a cutting element having a cutting tip and a cut-off circuit for sensing an electrical parameter which varies in response to penetration of at least part of the cutting tip of said trocar device through the wall of a body cavity of a patient undergoing electrosurgery and or interrupting the connection between the trocar device and the power source responsive to a variation in said parameter indicative of said penetration, said cutting element being connected to said power source through a current carrying conductor of a cable presenting a leakage impedance at the operating frequencies of said power source and said system further including means for counteracting the effect of the leakage impedance presented by the cable so that the electrical parameter sensed by said cut-off circuit is substantially free of the effect of said leakage impedance.

6. A system as claimed in claim 5 wherein said means comprising a reference conductor incorporated in said cable and arranged so as to extend along said current carrying conductor.

7. A system as claimed in claim 6, wherein said reference conductor and said current carrying conductor are connected to said source through a current transformer having a transformer core and are wound in opposition on the transformer core.

8. A system as claimed in claim 5 wherein said reference conductor is arranged so as to be permanently electrically disconnected from the cutting element of the trocar device.

* * * * *